United States Patent
Meadows et al.

(10) Patent No.: US 9,594,009 B2
(45) Date of Patent: Mar. 14, 2017

(54) CEMENT TESTING

(71) Applicant: Halliburton Energy Services, Inc., Houston, TX (US)

(72) Inventors: David L. Meadows, Marlow, OK (US); Robert P. Darbe, Duncan, OK (US); Keith D. Pewitt, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 410 days.

(21) Appl. No.: 14/166,497

(22) Filed: Jan. 28, 2014

(65) Prior Publication Data

US 2014/0137660 A1    May 22, 2014

Related U.S. Application Data

(62) Division of application No. 12/607,560, filed on Oct. 28, 2009, now Pat. No. 8,783,091.

(51) Int. Cl.
*G01N 3/08* (2006.01)
*G01N 3/12* (2006.01)
*G01N 33/38* (2006.01)

(52) U.S. Cl.
CPC .............. *G01N 3/08* (2013.01); *G01N 3/12* (2013.01); *G01N 33/383* (2013.01); *G01N 2203/0019* (2013.01); *G01N 2203/0048* (2013.01)

(58) Field of Classification Search
CPC ... G01N 2203/0019; G01N 2203/0048; G01N 33/383; G01N 3/08; G01N 3/12
See application file for complete search history.

(56) References Cited

U.S. PATENT DOCUMENTS

| | | |
|---|---|---|
| 2,662,827 A | 12/1953 | Clark |
| 3,541,845 A | 11/1970 | Kierkegaard-Hansen |
| 3,574,281 A | 4/1971 | Casey et al. |
| 3,619,463 A | 11/1971 | Budin et al. |
| 3,779,085 A | 12/1973 | Rice |
| 4,138,892 A | 2/1979 | Davis |
| 4,182,191 A | 1/1980 | Ikeda |
| 4,259,868 A | 4/1981 | Rao et al. |
| 4,377,087 A | 3/1983 | Rodot |
| 4,389,896 A | 6/1983 | Babcock |

(Continued)

FOREIGN PATENT DOCUMENTS

| | | |
|---|---|---|
| EP | 0 124 383 A1 | 11/1984 |
| EP | 0 101 580 B1 | 12/1986 |

(Continued)

OTHER PUBLICATIONS

Bridgman, P. W., "V. Breaking Tests Under Hydrostatic Pressure and Conditions of Rupture", Philosophical Magazine and Journal of Science, vol. 24, Sixth Series, pp. 63-80, (1912).

(Continued)

*Primary Examiner* — Daniel S Larkin
(74) *Attorney, Agent, or Firm* — John W. Wustenberg; Parker Justiss P.C.

(57) ABSTRACT

Devices and methods for testing cement include: a pressure vessel with a sample container inside an interior working volume of the pressure vessel, the pressure vessel configured to supply a first pressurized fluid to control a pore pressure of a cement sample and to supply a second pressurized fluid to lateral exterior surfaces of the sample container to provide a confining pressure that can be different than the pore pressure.

14 Claims, 7 Drawing Sheets

(56) References Cited

U.S. PATENT DOCUMENTS

| | | |
|---|---|---|
| 4,408,489 A | 10/1983 | Spangle |
| 4,430,889 A | 2/1984 | Sutton |
| 4,487,056 A | 12/1984 | Wiley |
| 4,491,017 A | 1/1985 | Iyer |
| 4,538,452 A | 9/1985 | Hrvojic |
| 4,567,759 A | 2/1986 | Ekstrom et al. |
| 4,567,765 A | 2/1986 | Rao et al. |
| 4,573,342 A | 3/1986 | Jones |
| 4,607,530 A | 8/1986 | Chow |
| 4,648,264 A | 3/1987 | Freese et al. |
| 4,685,092 A | 8/1987 | Dumont |
| 4,691,558 A | 9/1987 | Vinson et al. |
| 4,703,427 A | 10/1987 | Catala et al. |
| 4,757,479 A | 7/1988 | Masson et al. |
| 4,809,237 A | 2/1989 | Vogel et al. |
| 4,823,594 A | 4/1989 | Gray |
| 4,848,145 A | 7/1989 | Blaschke et al. |
| 4,893,285 A | 1/1990 | Masson et al. |
| 4,896,303 A | 1/1990 | Leslie et al. |
| 4,970,695 A | 11/1990 | Huau |
| 5,009,512 A | 4/1991 | Lessi et al. |
| 5,036,709 A | 8/1991 | McRae |
| 5,089,989 A | 2/1992 | Schmidt et al. |
| 5,127,473 A | 7/1992 | Harris et al. |
| 5,159,828 A | 11/1992 | Steiger |
| 5,216,638 A | 6/1993 | Wright |
| 5,226,310 A | 7/1993 | Steiger |
| 5,233,863 A | 8/1993 | Surjaatmadja et al. |
| 5,248,200 A | 9/1993 | Walsh |
| 5,325,723 A | 7/1994 | Meadows et al. |
| 5,346,012 A | 9/1994 | Heathman et al. |
| 5,353,637 A | 10/1994 | Plumb et al. |
| 5,368,103 A | 11/1994 | Heathman et al. |
| 5,377,160 A | 12/1994 | Tello et al. |
| 5,377,753 A | 1/1995 | Haberman et al. |
| 5,389,706 A | 2/1995 | Heathman et al. |
| 5,412,990 A | 5/1995 | D'Angelo et al. |
| 5,487,307 A | 1/1996 | Landgren et al. |
| 5,488,994 A | 2/1996 | Laurel et al. |
| 5,544,704 A | 8/1996 | Laurel et al. |
| 5,571,951 A | 11/1996 | Jamth |
| 5,572,021 A | 11/1996 | Heathman et al. |
| 5,696,059 A | 12/1997 | Onan et al. |
| 5,712,431 A | 1/1998 | Vilendrer |
| 5,718,292 A | 2/1998 | Heathman et al. |
| 5,741,971 A | 4/1998 | Lacy |
| 5,763,773 A | 6/1998 | Birchak et al. |
| 5,783,822 A | 7/1998 | Buchanan et al. |
| 5,787,983 A | 8/1998 | Heathman et al. |
| 5,836,200 A | 11/1998 | Belonenko et al. |
| 5,869,750 A | 2/1999 | Onan et al. |
| 5,964,293 A | 10/1999 | Chatterji et al. |
| 5,968,255 A | 10/1999 | Mehta et al. |
| 5,969,059 A | 10/1999 | Murai et al. |
| 5,972,103 A | 10/1999 | Mehta et al. |
| 5,992,223 A | 11/1999 | Sabins et al. |
| 5,996,693 A | 12/1999 | Heathman |
| 6,019,835 A | 2/2000 | Chatterji et al. |
| 6,053,245 A | 4/2000 | Haberman |
| 6,055,874 A | 5/2000 | Onan et al. |
| 6,060,434 A | 5/2000 | Sweatman et al. |
| 6,070,662 A | 6/2000 | Ciglenec et al. |
| 6,112,599 A | 9/2000 | Maki, Jr. |
| 6,124,246 A | 9/2000 | Heathman et al. |
| 6,134,954 A | 10/2000 | Suresh et al. |
| H1932 H | 1/2001 | Heathman et al. |
| 6,170,575 B1 | 1/2001 | Reddy et al. |
| 6,209,646 B1 | 4/2001 | Reddy et al. |
| 6,227,039 B1 | 5/2001 | Te'eni |
| 6,227,294 B1 | 5/2001 | Chatterji et al. |
| 6,245,142 B1 | 6/2001 | Reddy et al. |
| 6,258,757 B1 | 7/2001 | Sweatman et al. |
| 6,269,684 B1 | 8/2001 | Maki, Jr. et al. |
| 6,270,565 B1 | 8/2001 | Heathman |
| 6,345,535 B1 | 2/2002 | Sabins et al. |
| 6,367,549 B1 | 4/2002 | Chatterji et al. |
| 6,367,550 B1 | 4/2002 | Chatterji et al. |
| 6,379,456 B1 | 4/2002 | Heathman et al. |
| 6,444,316 B1 | 9/2002 | Reddy et al. |
| 6,454,001 B1 | 9/2002 | Thompson et al. |
| 6,478,868 B1 | 11/2002 | Reddy et al. |
| 6,478,869 B2 | 11/2002 | Reddy et al. |
| 6,484,568 B1 | 11/2002 | Griffith et al. |
| 6,494,951 B1 | 12/2002 | Reddy et al. |
| 6,510,743 B2 | 1/2003 | McAfee et al. |
| 6,527,051 B1 | 3/2003 | Reddy et al. |
| 6,527,438 B2 | 3/2003 | Zollinger et al. |
| 6,547,871 B2 | 4/2003 | Chatterji et al. |
| 6,554,071 B1 | 4/2003 | Reddy et al. |
| 6,591,910 B1 | 7/2003 | Chatterji et al. |
| 6,595,068 B2 | 7/2003 | Brovold et al. |
| 6,610,139 B2 | 8/2003 | Reddy et al. |
| 6,644,402 B1 | 11/2003 | Sharma et al. |
| 6,655,213 B1 | 12/2003 | Reinhardt et al. |
| 6,660,080 B2 | 12/2003 | Reddy et al. |
| 6,711,941 B2 | 3/2004 | Braithwaite et al. |
| 6,762,156 B2 | 7/2004 | Heathman et al. |
| 6,767,867 B2 | 7/2004 | Chatterji et al. |
| 6,782,735 B2 | 8/2004 | Walters et al. |
| 6,789,621 B2 | 9/2004 | Wetzel et al. |
| 6,797,054 B2 | 9/2004 | Chatterji et al. |
| 6,817,238 B2 | 11/2004 | Go Boncan et al. |
| 6,818,596 B1 | 11/2004 | Hayes |
| 6,828,922 B1 | 12/2004 | Gremmert et al. |
| 6,829,922 B2 | 12/2004 | Patin et al. |
| 6,834,233 B2 | 12/2004 | Economides et al. |
| 6,843,846 B2 | 1/2005 | Chatterji et al. |
| 6,874,353 B2 | 4/2005 | Johnson et al. |
| 6,892,814 B2 | 5/2005 | Heathman et al. |
| 6,910,535 B2 | 6/2005 | Tare et al. |
| 6,918,292 B2 | 7/2005 | Go Boncan et al. |
| 6,951,249 B1 | 10/2005 | Chatterji et al. |
| 6,964,302 B2 | 11/2005 | Luke et al. |
| 6,978,835 B1 | 12/2005 | Reddy et al. |
| 6,994,164 B2 | 2/2006 | Tare et al. |
| 7,004,256 B1 | 2/2006 | Chatterji et al. |
| 7,008,477 B2 | 3/2006 | Chatterji et al. |
| 7,013,975 B2 | 3/2006 | Chatterji et al. |
| 7,048,054 B2 | 5/2006 | Heathman et al. |
| 7,089,816 B2 | 8/2006 | Hakimuddin |
| 7,096,944 B2 | 8/2006 | Vargo, Jr. et al. |
| 7,128,142 B2 | 10/2006 | Heathman et al. |
| 7,128,149 B2 | 10/2006 | Heathman et al. |
| 7,143,827 B2 | 12/2006 | Chatterji et al. |
| 7,178,590 B2 | 2/2007 | Vargo, Jr. et al. |
| 7,191,663 B2 | 3/2007 | Go Boncan et al. |
| 7,222,676 B2 | 5/2007 | Patel et al. |
| 7,552,648 B2 | 6/2009 | McMechan et al. |
| 7,621,186 B2 | 11/2009 | Heathman et al. |
| 2001/0001381 A1 | 5/2001 | Reddy et al. |
| 2001/0037687 A1 | 11/2001 | Brovold |
| 2003/0140707 A1 | 7/2003 | Pyle et al. |
| 2003/0150263 A1 | 8/2003 | Economides et al. |
| 2003/0161211 A1 | 8/2003 | Duell et al. |
| 2003/0221829 A1 | 12/2003 | Patel et al. |
| 2004/0054262 A1 | 3/2004 | Horak |
| 2004/0055392 A1 | 3/2004 | Patin et al. |
| 2004/0154263 A1 | 8/2004 | Li et al. |
| 2004/0221990 A1 | 11/2004 | Heathman et al. |
| 2004/0226483 A1 | 11/2004 | Chatterji et al. |
| 2005/0009710 A1 | 1/2005 | Heathman et al. |
| 2005/0080161 A1 | 4/2005 | Tare et al. |
| 2005/0109507 A1 | 5/2005 | Heathman et al. |
| 2005/0126300 A1 | 6/2005 | Go Boncan et al. |
| 2005/0135185 A1 | 6/2005 | Duell et al. |
| 2005/0152432 A1 | 7/2005 | Hakimuddin |
| 2005/0204960 A1 | 9/2005 | Heathman et al. |
| 2006/0000612 A1 | 1/2006 | Reddy et al. |
| 2006/0225523 A1 | 10/2006 | Reddy et al. |
| 2006/0258545 A1 | 11/2006 | Chatterji et al. |
| 2007/0012441 A1 | 1/2007 | Heathman et al. |
| 2007/0056383 A1 | 3/2007 | Deeg |
| 2007/0082822 A1 | 4/2007 | Kirsner et al. |
| 2007/0105995 A1 | 5/2007 | Chatterji et al. |

(56) References Cited

U.S. PATENT DOCUMENTS

| | | |
|---|---|---|
| 2007/0169937 A1 | 7/2007 | Allin et al. |
| 2007/0173412 A1 | 7/2007 | Allin et al. |
| 2008/0168848 A1 | 7/2008 | Funkhouser et al. |
| 2008/0178683 A1 | 7/2008 | Heathman et al. |
| 2008/0197605 A1 | 8/2008 | Blaschke et al. |
| 2009/0084189 A1 | 4/2009 | McMechan et al. |
| 2011/0061525 A1 | 3/2011 | Gray et al. |
| 2013/0228019 A1 | 9/2013 | Meadows et al. |
| 2014/0007695 A1 | 1/2014 | Darbe et al. |

FOREIGN PATENT DOCUMENTS

| | | |
|---|---|---|
| EP | 0 110 750 B1 | 9/1988 |
| EP | 0 098 778 B1 | 3/1989 |
| EP | 0 198 985 B1 | 12/1989 |
| EP | 0 443 936 A1 | 8/1991 |
| EP | 0 395 499 B1 | 7/1993 |
| EP | 1 189 051 | 2/2001 |
| EP | 0 865 612 B1 | 6/2002 |
| EP | 1 541 987 | 6/2005 |
| FR | 2 340 551 | 9/1977 |
| FR | 2 746 920 | 10/1997 |
| GB | 2 353 546 A | 2/2001 |
| GB | 2 354 026 A | 3/2001 |
| GB | 2 355 742 A | 5/2001 |
| GB | 2 386 625 A | 9/2003 |
| WO | WO 00/49273 | 8/2000 |
| WO | WO 2004/008302 A1 | 10/2004 |
| WO | WO 2005/065411 | 7/2005 |
| WO | WO 2008/084201 | 7/2008 |
| WO | WO 2010/094925 | 8/2010 |

OTHER PUBLICATIONS

"Standard Test Method for Tensile Strength of Hydraulic Cement Mortars", ASTM Standards, C-190-85, pp. 197-202, (1985).

Clayton, N. et al., "The Diphase Concept, With Particular Reference to Concrete", *Developments in Concrete Technology*, vol. 1, F. D. Lydon, Ed.: Applied Science Publisher Ltd, Chapter 7, pp. 283-318, (1979).

Clayton, N., "Fluid-pressure Testing of Concrete Cylinders," *Magazine of Concrete Research*, vol. 30, No. 102, pp. 26-30, (1978).

Deeg, Wolfgang, et al., "*How Foamed Cement Advantages Extend to Hydraulic Fracturing Operations*," World Oil, Nov. 1999, pp. 51-53.

Dillenbeck, R.L., GoBoncan, V., and Rogers, M.J., "*Testing Cement Static Tensile Behavior Under Downhole Conditions*," SPE 97967, Society of Petroleum Engineers, Copyright 2005, 12 pages.

FlexiForce®, materials downloaded from Tekscan website (www.tekscan.com) on FlexiForce® sensors), http://www.tekscan.com/flexiforce.html, visited Aug. 3, 2005, 20 pages.

Goodwin, K.J., "*Cement Sheath Stress Failure*," SPE Drilling Engineering, SPE 20453, Dec. 1992, pp. 291-296, and additional pp. 501-508 from SPE 20453.

Love, A.E.H., "*A Treatise on the Mathematical Theory of Elasticity*," Fourth Edition, Dover Publications, New York, 1944, pp. 144-145.

Mindess, S. et al., "The Nitrogen Gas Tension Test of Concrete", Proceedings of ConMat '05 and Mindess Symposium, Aug. 22-24, 2005, The University of British Columbia, Vancouver, Canada, 8 pages, (2005).

Minear, John W. and Goodwin, K. Joe, "*Cement-Sheath Evaluation*," Chapter 10, Petroleum Well Construction, John Wiley & Sons Publisher, ISBN 0-471-96938-9, copyright 1998, front and back cover and pp. 271-296.

Richart, Frank E. et al., "A Study of the Failure of Concrete Under Combined Compressive Stresses", The University of Illinois—Engineering Experiment Station, Bulletin No. 185, pp. 3-253, (1928).

Sabins, Fred, "MMS Project Long-Term Integrity of Deepwater Cement Systems Under Stress/Compaction Conditions", CSI Technologies, Sep. 3, 2004.

Thiercelin, J.J., et al., "Cement Design Based on Cement Mechanical Response," *SPE Drilling & Completion*, Society of Petroleum Engineers, SPE 52890, Dec. 1998, pp. 266-273.

Authorized officer Athina Nickitas-Etienne, International Preliminary Report on Patentability in International application No. PCT/GB2010/002001, mailed Dec. 6, 2012, 7 pages [Corresponding PCT case].

International Search Report and Written Opinion for International Application No. PCT/GB2010/002001, mailed Nov. 19, 2012, 10 pages.

EPO Communication, Extended European Search Report, EP 14191957.1-1558, Jan. 16, 2015, 4 pages.

CEMENT TESTING

CROSS REFERENCE TO RELATED APPLICATION

This application claims priority to, and is a divisional of, U.S. patent application Ser. No. 12/607,560, entitled "Cement Testing," filed on Oct. 28, 2009, now U.S. Pat. No. 8,783,091, the entire contents of which is incorporated by reference herein.

TECHNICAL FIELD

This disclosure relates to measuring mechanical properties.

BACKGROUND

Some well bores, for example some oil and gas wells, are lined with a casing. The cemented casing stabilizes the sides of the well bore, prevents fluids (liquids or gases) in the well bore from entering the surrounding earth formations, and/or prevents fluids from zones other than the producing zones from entering the well bore.

In a typical cementing operation, cement is introduced down the well bore and into an annular space between the casing and the surrounding earth. The cement secures the casing in the well bore, and prevents fluids from flowing vertically in the annulus between the casing and the surrounding earth.

Different cement formulations are designed for a variety of well bore conditions, which may be above ambient temperature and pressure. In designing a cement formulation, a number of potential mixtures may be evaluated to determine their mechanical properties under various conditions.

Mechanical properties of subterranean formations in which well bores are to be formed can also affect the design of the well bores. In some instances, samples of subterranean formations are taken and subsequently evaluated to determine the mechanical properties of the formations.

SUMMARY

Using the devices and methods described, cement samples can be cured at downhole conditions and the curing or cured sample subjected to tests including direct pull tensile strength tests without removal from the pressure vessel being used to maintain downhole conditions. This enables the application of drained or undrained unconfined compressive testing conditions, drained or undrained confined compressive testing conditions, drained or undrained unconfined tensile testing conditions, and drained or undrained confined tensile testing conditions as well as hydrostatic test conditions and derivatives.

In addition, cement samples can be tested while controlling both the pore pressure within the cement sample and the confining pressure applied to lateral exterior surfaces of a cement sample. This can allow, for example, the pore pressure to be controlled separately from the confining pressure. Accordingly, the pore pressure can be maintained at the curing pressure, set equal to the confining pressure, or set at another arbitrary value. This allows the user replicate tests with different pore and confining pressures to verify that the tensile strength/compressive strength of the sample is not affected by the relationship between pore and confining pressures.

In one aspect, systems for testing cement include at least one cement testing apparatus. The cement testing apparatus includes: a pressure vessel defining: a working volume inside the pressure vessel, the pressure vessel defining a first channel providing liquid communication through the pressure vessel to the working volume of the pressure vessel and a second channel providing liquid communication through the pressure vessel to the working volume of the pressure vessel; and a substantially tubular sample container defining a sample volume inside the sample container, the sample container comprising walls extending from a first end with an opening to a second end with an opening, the sample container disposed in the working volume of the pressure vessel with the sample container substantially sealed to prevent liquid communication between the sample volume of the sample container and portions of the working volume of the pressure vessel outside the sample container. The sample container is positioned such that the first channel provides liquid communication through the pressure vessel to the sample volume of the sample container; and the second channel provides liquid communication through the pressure vessel to the portions of the working volume of the pressure vessel outside the sample container.

In one aspect, devices for testing cement include: a pressure vessel with a sample container inside an interior working volume of the pressure vessel, the pressure vessel configured to supply a first pressurized fluid to control a pore pressure of a cement sample and to supply a second pressurized fluid to lateral exterior surfaces of the sample container to provide a confining pressure that can be different than the pore pressure.

Embodiments can include one or more of the following features.

In some embodiments, the sample container includes: a first end member; a second end member; and a tubular member having walls that substantially sealed to the first end member and the second end member, the tubular member substantially more flexible than the first and second end members.

In some embodiments, the end members are configured to grip ends of a cement sample in the sample container. In some cases, each of the end members of the sample container defines an internal cavity that has a transverse first cross-sectional dimension adjacent the tubular member and a second transverse cross-section spaced apart from tubular member that is larger than the first cross-sectional dimension.

In some embodiments, the first end member of the sample container has a face extending across a first open end of the tubular member, the first end member defining a channel in liquid communication with the channel defined in the first end cap of the pressure vessel and extending to an opening in the face of the first end member. In some cases, the second end member has a face extending across a second open end of the tubular member, the second end member defining a frusto-conical cavity extending from an opening in the face of the second end member.

In some embodiments, the pressure vessel includes: a first end cap; a second end cap; and a sidewall member extending between the first end cap and the second end cap. In some cases, the first end cap of the pressure vessel defines the first channel through the end cap to the interior volume of the pressure vessel. The second end cap can define a third channel extending through the second end cap. In some cases, the piston extends through an aperture in the second end cap of the pressure vessel. The piston can define a channel extending through the piston, the channel in the piston providing liquid communication between an exterior of the pressure vessel and the second end member of the sample container.

In some embodiments, the at least one cement testing apparatus comprising a plurality of the cement testing apparatuses. In some cases, systems also include: a first pressure source operable to selectively supply pressurized liquid to the first channels of the plurality of cement testing apparatuses; and a second pressure source operable to selectively supply pressurized liquid to the second channels of the plurality of cement testing apparatuses.

In some embodiments, devices also include a piston which can apply tension or compression along an axis of the cement sample.

In one aspect, methods of testing cement include: controlling pore pressure in a cement sample inside a sample container disposed in a pressure vessel of a testing apparatus while the cement sample is curing to provide a first pressure in the cement sample; and simultaneously controlling a confining pressure applied to lateral exterior surfaces of the sample container to provide a second pressure that can be different than the first pressure. Embodiments can include one or more of the following features.

In some embodiments, methods also include: mixing a slurry of the cement sample at pressure conditions that are different than ambient pressure conditions; and transferring the slurry of the cement sample to the sample container for curing without exposure to ambient pressure conditions.

In some embodiments, methods also include: selecting end caps of the sample container based on tests to be performed; assembling the sample container by attaching the end caps to opposite ends of a substantially tubular sleeve which is more flexible than the end caps; and filling the sample container with slurry.

In some embodiments, methods also include: simultaneously setting initial pressure and/or temperature conditions in multiple testing apparatuses; isolating at least one of the testing apparatuses from others of the multiple testing apparatuses; and testing a mechanical property of cement sample(s) in the at least one of the testing apparatuses isolated from others of the multiple testing apparatuses. In some cases, methods also include: calculating a failure mode for the cement being tested based on testing a mechanical property of the cement sample in each of the multiple testing apparatuses.

In some embodiments, methods also include: curing a cement sample at first pressure conditions that are different than ambient conditions; and pulling on ends of the sample to apply axial tension to the sample while maintaining the sample at the first pressure conditions.

The methods and systems described can provide one or more of the following advantages.

The methods and systems described can allow a liquid slurry to cure at pressure and temperature conditions and, while curing or after cured, to be tested for volume changes, the mechanical response of the sample, and failure limits without removing curing, or cured, cement from the testing apparatus. Testing in the curing vessel can reduce the possibility that removal of the sample from the testing apparatus could impart damage to the sample that would influence subsequent results. Testing in the curing vessel can also save time and money, and reduces the limits on the ability to test curing in a small time window relative to cure associated with systems which require removal of the curing vessel for testing.

The methods and systems described can allow for independent control over pore pressure, confining pressure, and load magnitude, direction, and rate. In combination, the independent control of these parameters allows for multiple samples to be tested in replicate and with changes to one parameter at a time to provide statistics as well as different testing conditions.

The methods and systems described can provide the ability to cure and test cement at conditions that represent a cemented well casing.

The details of one or more embodiments are set forth in the accompanying drawings and the description below.

DETAILED DESCRIPTION

The devices and methods described herein can allow an accurate measurement of mechanical properties and behaviors of cement formulations including, for example, tensile strength, compressive strength, shrinkage, and other properties. For example, a sample cement composition can be cured or partially cured at downhole conditions (e.g., temperatures and/or pressures elevated above ambient conditions) while monitoring chemical and bulk shrinkage and, at a specified time, changing the stress conditions applied to the sample while monitoring the mechanical response until failure occurs. Mechanical properties of the cement sample can be calculated based on the response of the sample to the differential stress conditions while the failure limits established by the material response or maximum stress endured before failure.

As used herein, "cement" and "cement composition" encompass a fluid mixture that hardens into solid, and may be any agent suitable to bond casing or other tubulars to well bore walls or to other tubing used for downhole applications. Some examples of cement include hydraulic cement (e.g., Portland cement formulations) and non-hydraulic cement (e.g., polymer resin formulations). As used herein, "curing" refers to the reactions through which cement hardens from a fluid mixture into a solid. In some instances, the devices and methods discussed herein can be used to measure mechanical properties at temperatures and pressures that simulate downhole conditions.

As used herein, "tube" and "tubular" encompass hollow members (e.g., hollow members made of metal, glass, rubber, or other material) with open ends. Such hollow members can be, but are not necessarily, cylindrical in shape.

As used herein, "piston" encompasses driving mechanisms including, for example, hydraulic pistons, power screws, linear actuators. Thus, the piston does not necessarily seal against the pressure vessels described below.

Figure 1:
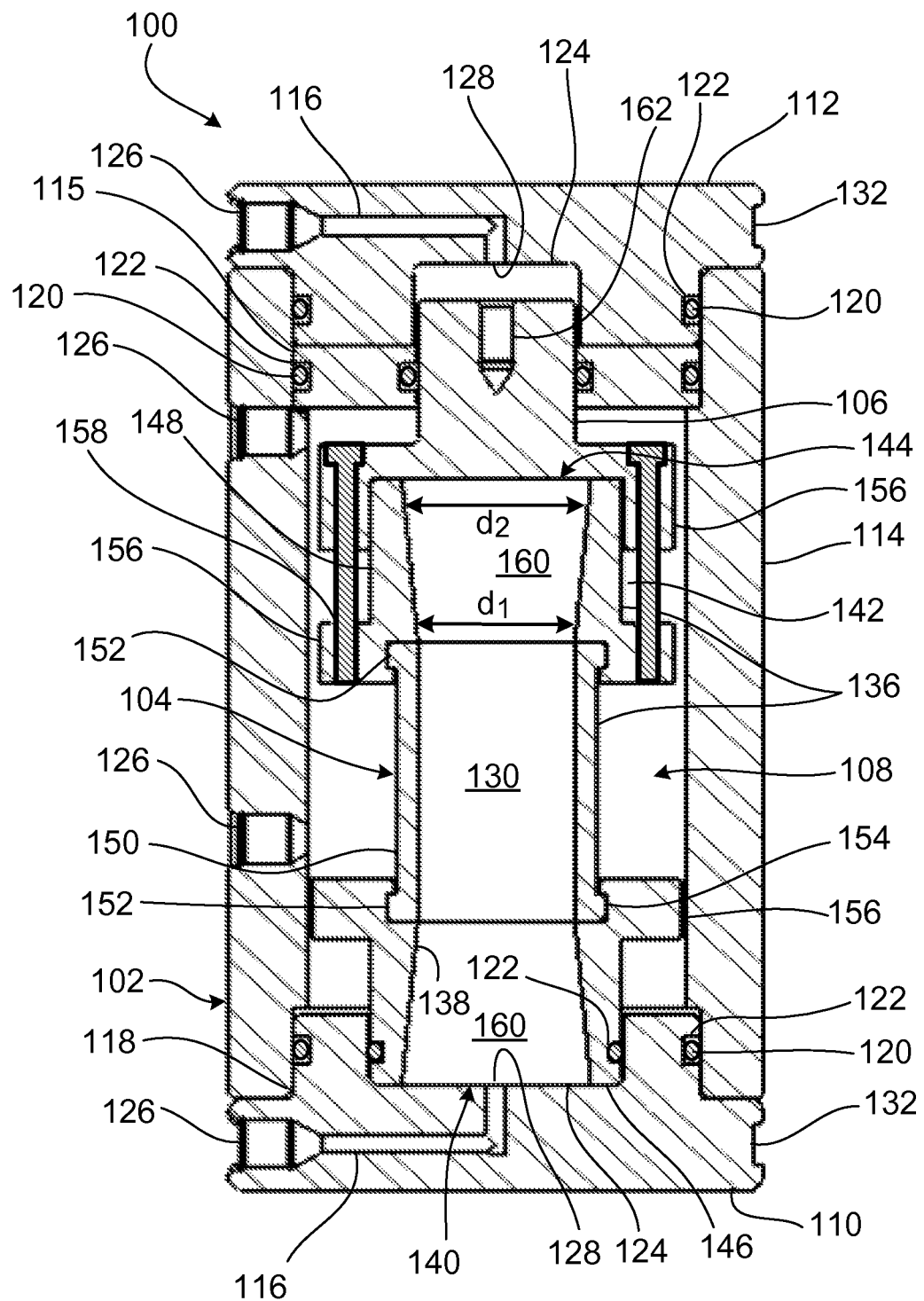
FIG. 1 is a cross-section of a cement testing apparatus.

Referring to FIG. 1, a cement testing apparatus 100 that includes a pressure vessel 102, a sample container 104, and a piston 106 can be configured for testing the tensile strength of a cement sample. The illustrated testing apparatus 100 is substantially cylindrical in shape. However, in some embodiments, the testing apparatus 100 can have other shapes (e.g., can be substantially rectangular in shape). The modular nature of the pressure vessel 102 and the sample container 104 can facilitate providing different testing apparatus configurations. For example, the configuration illustrated in FIG. 1 can be used to test the tensile strength of a cement sample. As discussed in more detail below, the cement testing apparatus 100 can be configured for testing compression strength of the cement sample by choosing different components and configurations.

The pressure vessel 102 can have an interior working volume 108 defined by a first end cap 110, a second end cap 112, and sidewall member 114 formed by a hollow cylinder extending between the end caps 110, 112. The pressure vessel 102 can also include an isolation ring 115.

The first end cap 110 defines a channel 116 extending through the first end cap 110. The end cap 110 includes a shoulder 118 configured for press-fit engagement with sidewall member 114. A seal 120 (e.g., an O-ring) is disposed in groove 122 and can limit (e.g., substantially prevent) leakage between the first end cap 110 and the sidewall member 114. In some cases, a seal 120 such as an O-ring is disposed of in a groove 122 formed in the sidewall member 114 rather than in the first end cap 110. In some cases, pressure vessels can use other sealing mechanisms including, for example, matching threads or metal-to-metal seals.

A bore 124 formed in the inner side of the first end cap 110 is sized to receive the lower end of the sample container 104. The channel 116 in the first end cap 110 extends from a port 126 formed in a surface of the first end cap 110 to an opening 128 which provides liquid communication with an internal working volume 108 of the pressure vessel 102. The opening 128 is positioned to provide liquid communication with an interior sample volume 130 of the sample container 104 when the sample container 104 is installed in the pressure vessel 102. In the illustrated embodiment, the opening 128 is positioned in the center of the bore 124. Some embodiments include more than one opening 128 and/or grooves along the face of bore 124 to distribute the fluid being used to control the pore pressure of the sample.

The port 126 can be configured to receive the end fitting (not shown) of tubing to convey fluid from a pressure source to the channel 116. In some situations, a plug (not shown) can be used to substantially seal the port 126. A slight groove 132 can be formed extending around part or all of the lateral outer surface of the first end cap 110. The groove 132 can facilitate handling and sealing the pressure vessel 102.

Terms of relative orientation such as upper, lower, above, and below are used relative to the orientation of embodiments shown in the figures being discussed. Although such terms do not require that the illustrated devices be oriented as shown in the figures, the cement testing apparatus 100 will typically be oriented as shown in FIG. 1 during use.

In the illustrated embodiment, the second end cap 112 is substantially similar to the first end cap 110. The second end cap 112 includes a channel 116 extending from port 126 to opening 128. The primary difference between the first end cap 110 and the second end cap 112 is that the bore 124 formed in the second end cap 112 is sized to receive a portion of the piston 106 where the bore 124 in the first end cap 110 is sized to receive the lower end of the sample container 104.

The sidewall member 114 is attached to the end caps 110, 112 by pressfit engagement between the sidewall member 114 and the end caps 110, 112. This configuration provides for easy assembly and disassembly of the pressure vessel 102. However, this configuration can require an external locking mechanism (not shown) to hold the pressure vessel 102 together as a pressurizing fluid is supplied to the interior volume 108 of the pressure vessel. In some embodiments, the end caps 110, 112 and the sidewall member 114 have matching threads on the exterior surfaces of the end caps 110, 112 and the corresponding to interior surfaces of the sidewall member 114. In these embodiments, the end caps 110, 112 and the sidewall member 114 can be screwed together. Alternatively, the end caps 110, 112 and the sidewall member 114 can also be attached using J-lock attachment mechanisms.

The sidewall member 114 can define two ports 126 with the upper port 126 positioned at or near the upper end of the interior volume 108 of the pressure vessel 102. The ports 126 defined by the sidewall member 114 act as channels providing liquid communication through the pressure vessel 102 to the working volume of the pressure vessel. The ports 126 defined by the sidewall member 114 are positioned such that the ports 126 in the sidewall member 114 provide liquid communication through the pressure vessel 102 to the portions of the working volume 108 of the pressure vessel 102 outside the sample container 104 when the sample container 104 is installed in the pressure vessel 102. The upper port 126 can be used to bleed off one fluid (e.g., air) while the interior volume 108 of the pressure vessel 102 is being filled with a denser second fluid (e.g., a petroleum based pressurizing fluid or water).

The isolation ring 115 has O-ring 120/groove 122 combinations to limit fluid flow both between the isolation ring 115 and the sidewall member 114 and between the isolation ring 115 and the piston 106. In some embodiments, rather than being a separate component, the isolation ring 115 is incorporated as part of the second end cap 112 of the pressure vessel 102.

During use, the temperature of fluid in the pressure vessel 102 can range from room temperature to the high temperatures associated with downhole conditions (e.g., up to 1000 degrees Fahrenheit). The pressure of the fluid in the pressure vessel can range from atmospheric pressure to the high pressures associated with downhole conditions (e.g., up to 50,000 psi). The components of the pressure vessel 102 can be made from materials which are strong (e.g., able to maintain structural stability when subjected to high pressures), are durable (e.g., resistant to corrosion by the anticipated pressurizing fluids in the anticipated temperature and pressure ranges), and can be formed with the precision necessary to maintain substantially pressure-tight engagement between the components under testing conditions. For example, the end caps 110, 112 and sidewall member 114 can be machined from stainless steel. Alternatively, the end caps 110, 112 and sidewall member 114 can be formed using casting, laminating, or molding techniques from materials including, for example, steel, alloys, or composite fibers with a resin structure.

The sample container 104 includes walls 136 extending from a first end 138 with an opening 140 to a second end 142 with an opening 144. The walls 136 defined the interior sample volume 130 of the sample container 104. The sample container 104 has a substantially tubular shape. The sample container 104 can be disposed in the working volume 108 of the pressure vessel 102 with the sample container 104 substantially sealed to prevent liquid communication between the sample volume 130 of the sample container 104 and portions of the working volume 108 of the pressure vessel 102 outside the sample container 104. For example, the walls 136 of the sample container 104 illustrated in FIG. 1 are formed by a first end member 146, a second end member 148, and a tubular member 150 having walls that can be substantially sealed to the first end member 146 and the second end member 148. The tubular member 150 is more flexible than the first and second end members 146, 148. For example, in the embodiment illustrated in FIG. 1, the tubular member 150 can be formed of rubber and the first and second end members 146, 148 can be formed of stainless steel. The first and second end members 146, 148 have grooves 152 formed extending into inner surfaces of the end members 146, 148. The grooves 152 are sized and configured to receive flanges 154 extending outwards from the ends of the tubular member 150. Engagement between the grooves 152 of the first and second end members 146, 148 and the flanges 154 of the tubular member 150 both provides a seal between and holds together the end members 146, 148 and the tubular member 150. Some embodiments use other methods of attachment including, for example, pressfit engagement, threaded engagement, or J-lock attachment mechanisms.

The lower end of the first end member 146 is received in the bore 124 of the first end cap 110. The lower end of the first end member 146 receives a seal 120 (e.g., an O-ring) disposed in the groove 122 formed in an outer surface of the first end member 146. In some cases, the seal 120 can be disposed of in a groove 122 formed in the inner surface of the sidewall member 114 rather than in the outer surface of the first end cap 110.

The upper end of the first end member 146 includes outwardly extending flanges 156. The outwardly extending flanges 156 of the first end member 146 do not, under normal conditions, contact the sidewall member 114. The outwardly extending flanges 156 of the first end member 146 of the sample container 104 and the first end cap of the pressure vessel 102 include corresponding multiple threaded bores which allow the first end member 146 of the sample container 104 to be bolted to the first end cap of the pressure vessel 102. These bores and bolts are not shown because they do not lie in the plane of the cross-section shown in FIG. 1. Some embodiments use other methods of attachment including, for example, pressfit engagement, threaded engagement, or J-lock attachment mechanisms.

The lower end of the second end member 148 also has outwardly extending flanges 156. The outwardly extending flanges 156 of the second end member 148 include multiple threaded bores 158 which allow the piston 106 to be bolted to the second end member 148 of the sample container 104. In the illustrated embodiment, no additional sealing mechanisms are provided to limit the flow of fluid between the piston 106 and the sample container 104. However, some embodiments include sealing mechanisms between the piston 106 and the sample container 104 such as the O-ring 120/groove 122 combination used elsewhere in the testing apparatus 100.

The end members 146, 148 are configured to grip ends of a cement sample in the sample container. For example, in the illustrated embodiment, the end members 146, 148 of the sample container 104 define an internal cavity 160 that is part of the sample volume 130 of the sample container 104. The internal cavities 160 of the end members 146, 148 each have a transverse first cross-sectional dimension d1 adjacent the tubular member 150 and a second transverse cross-section d2 spaced apart from tubular member 150 that is larger than the first cross-sectional dimension d1.

The end members 146, 148 can be machined from stainless steel. Alternatively, the end members 146, 148 end caps 110, 112 can be formed using casting, laminating, or molding techniques from materials including, for example, steel, alloys, or composite fibers with a resin structure. The tubular member 150 can be molded from rubber. Alternatively, the tubular member 150 can be formed using machining or laminating techniques from materials including, for example, epoxy or resins.

The piston 106 has a first end that receives the second end member 148 of the sample container 104 and a second end that is received by the isolation ring 115 and the bore 124 of the second end cap 112 of the pressure vessel 102. Threaded bores 156 in flanges extending outward from the first end of the piston allow the piston 106 to be bolted to the second end member 148 of the sample container 104. The second end of the piston 106 defines a threaded bore 162. The threaded bore 162 is provide to help in disassembling the apparatus. After testing, a threaded tool or bolt can be screwed into threaded bore 162 to provide a point of purchase for applying force to detach the piston 106 from the sample container 104. The piston can be machined from stainless steel. Alternatively, the piston 106 can be formed using casting, laminating, or molding techniques from materials including, for example, steel, alloys, or composite fibers with a resin structure.

Testing apparatuses can include sensors to measure parameters used to calculate properties of samples being tested. For example, testing apparatus 100 may include linear variable displacement transducers (LVDTs) positioned at 120 degree intervals around a circle around the end members 146, 148 of the sample container 104 or in other suitable positions. The average reading of the three LVDTs can be used to characterize the length change of the sample during testing. In addition, LVDTs can be used to measure tangential changes in deformation of the sample. Other sensors, such as extensometers, electrical strain gauges or fiber optic strain gauges, can be used in addition to or in place of the LVDTs to measure relevant parameters. For example, four strain gauges (two vertical and two tangential) could be attached to interior surfaces of tubular member 150 to provide material data that would be difficult to obtain otherwise. Alternatively, strain gauges could be attached to exterior surfaces of tubular member 150. Similarly, the amount of fluid (e.g., water) pumped into the pressure vessel 102 as the cement cures can provide a measure of cement shrinkage. Pressure and temperature sensors can be included to measure pressures and temperatures present during testing. Pressure, temperature, and strain sensors can be used as feedback to control the test process. For example, pressure sensors can control the pump to pressure up or down dependent upon a controlled set point. Likewise, the piston loading the test specimen can be actuated in a direction depending on the deflection or strain measurements experienced by the sample.

Temperature can be controlled to simulate downhole conditions during testing or at other times. For example, in testing cement, the testing apparatus 100 and cement slurry can be preheated during mixing. The desired temperature can be maintained as the sample cement composition cures using external heating elements (e.g., heater coils or stainless steel heater bands) or placing the testing apparatus 100 in an oven. Likewise the testing apparatus could also be heated in a profile that simulates the temperature a cement system would experience from mixing, placement, and curing during cementing a wellbore casing string.

Figure 2:
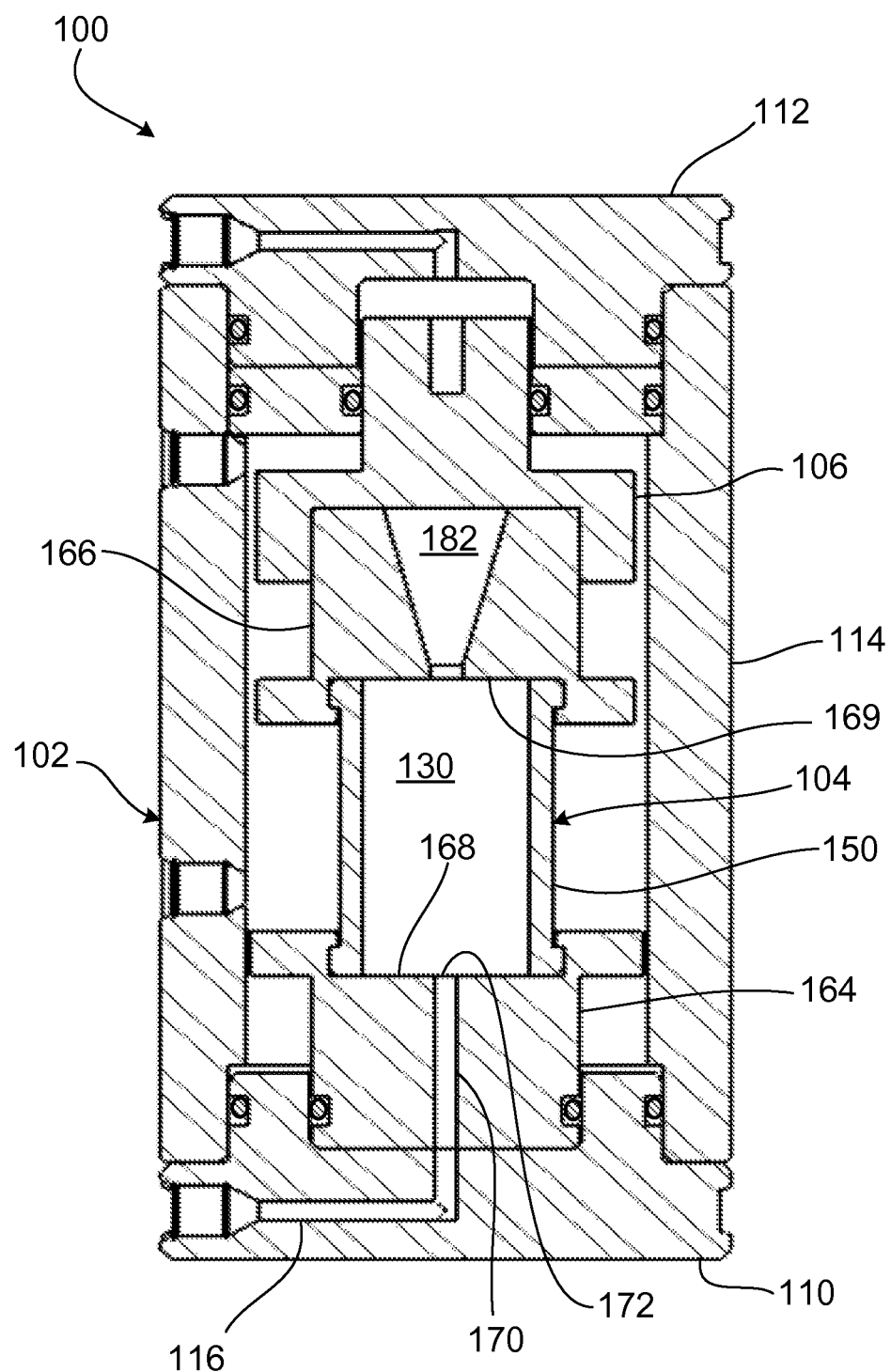
FIG. 2 is a cross-section of a cement testing apparatus.

As shown in FIG. 2, the cement testing apparatus 100 can also be configured for compression testing of a cement sample. In this configuration, the pressure vessel 102 can include the same end caps 110, 112 and sidewall member 114 described above with respect to FIG. 1. Sample container 104 can include the same tubular member 150 described above with respect to FIG. 1. The primary difference between configurations is that the sample container 104 includes different end members.

A first end member 164 of the sample container 104 has a face 168 extending across a first open end of the tubular member 150. The first end member 164 defines a channel 170 in liquid communication with the channel 116 defined in the first end cap 112 of the pressure vessel 102 and extending to an opening 172 in the face 168 of the first end member 164. The combined channels enable a pressure source (not shown) connected to the port and the first end cap 110 of the pressure vessel 102 to control the pore pressure of a cement sample in the sample volume 130 of the sample container 104. A second end member 166 of the sample container 104 has a face 169 extending across a second open end of the tubular member 150. The second end member 166 defines a buffer space which can be used to compensate for the expansion or contraction of a cement sample during hydration and/or curing. In the illustrated embodiment, the buffer space is a frusto-conical cavity extending from an opening in the face 169 of the second end member 166. In some cases, other shapes can be used.

Figure 3:
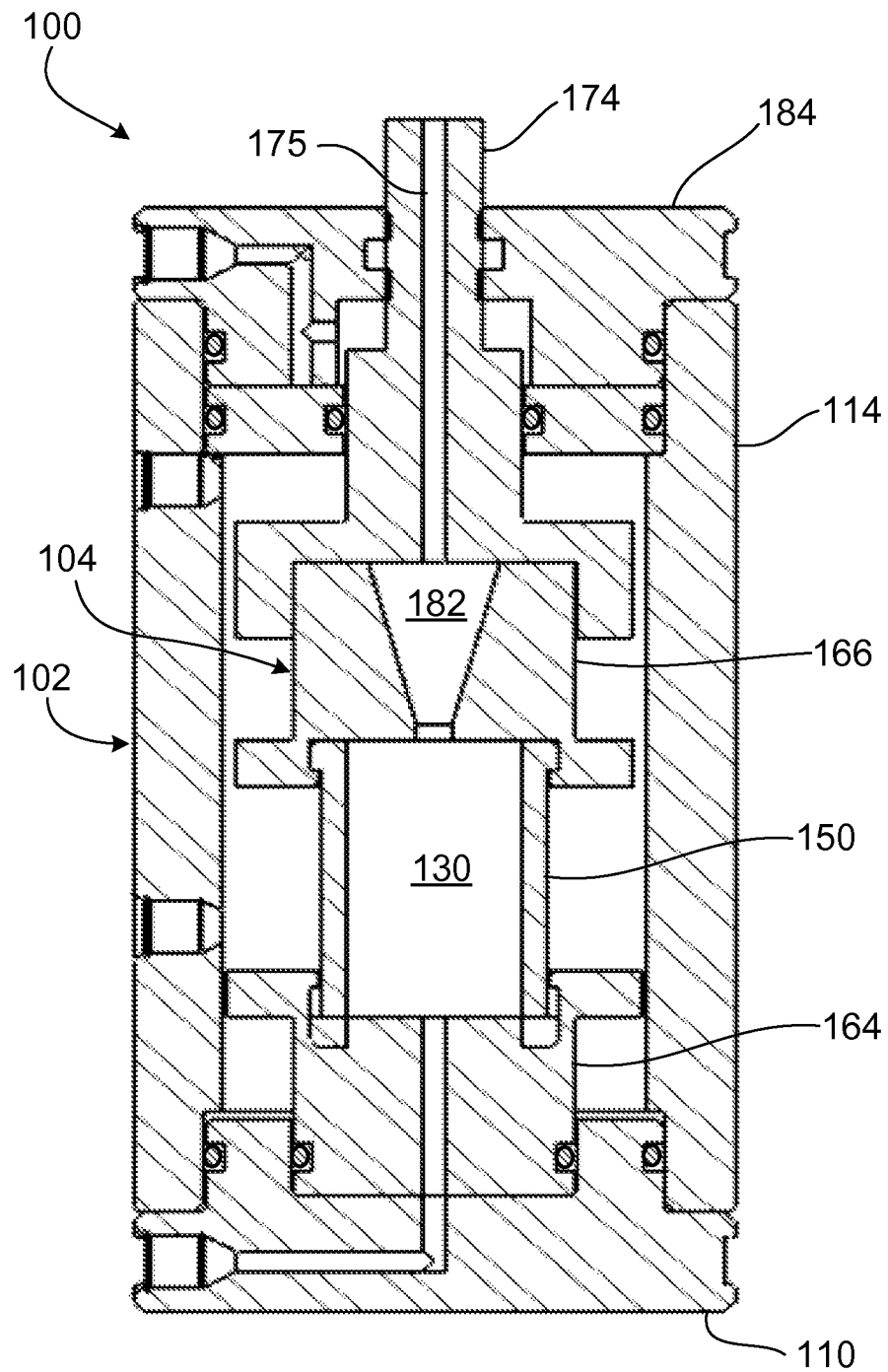
FIG. 3 is a cross-section of a cement testing apparatus.

As shown in FIG. 3, the cement testing apparatus 100 can also be configured such that a slurry of a cement sample can be mixed at pressure and temperature conditions that are different than ambient pressure conditions and then be transferred to the sample container for curing without exposure to ambient pressure conditions. In this configuration, the sample container 104 can include the same end members 164, 166 as described above with respect to FIG. 2. The primary difference between the configurations shown in FIG. 2 and in FIG. 3 is that a piston 174 has an end that extends through an aperture in a second end cap 184 of the pressure vessel 102. The piston 174 defines a channel 175 extending through the piston 174. The channel 175 in the piston 174 provides liquid communication between an exterior of the pressure vessel 102 and the second end member 166 of the sample container 104. In the illustrated embodiment, the channel 175 can discharge a cement slurry into the buffer space 182.

In the illustrated embodiment, the piston 174 is used in a cement testing apparatus 100 configured for testing the compressive strength of the cement sample. In some cases, a similar piston can be used in a cement testing apparatus 100 configured for testing the tensile strength of the cement sample. For example, the piston 174 and the end cap 184 of the pressure vessel 102 can be used in place of the piston 106 and the end cap 112 shown in FIG. 1.

The testing apparatus 100 can be used to perform a variety of tests on cement samples including, for example, tests for uniaxial compressive strength, triaxial compressive strength, uniaxial tensile strength, and hydrostatic strength. After determining which test a specific testing apparatus 100 will be used to perform, the appropriate components of the specific testing apparatus 100 are assembled and filled with a slurry of the cement to be tested.

Figure 4:
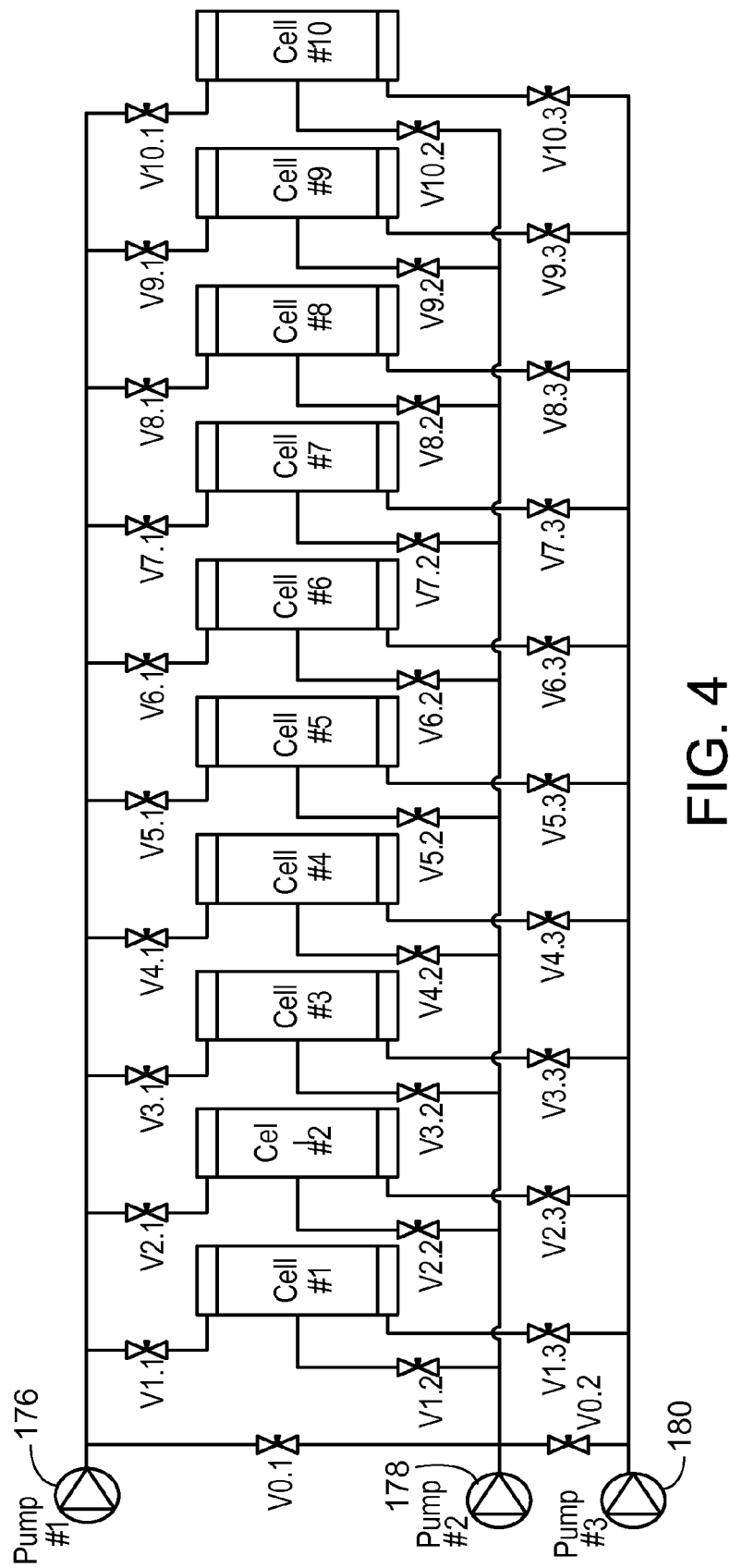
FIG. 4 is a schematic of a cement testing system with multiple cement testing apparatuses.

In some embodiments, systems can include multiple testing apparatuses 100 attached in parallel to three pressure sources (e.g., pumps 176, 178, 180) as shown in FIG. 4. The pump 176 can be used to apply the desired load for a specific test, the pump 178 can be used to control the confining pressure applied to lateral side surfaces of the sample, and the pump 180 can be used to control the pore pressure of the sample. Running specific tests on multiple testing apparatuses can provide the data necessary to run statistical analyses on the resulting strength and property measurements. Running different tests on multiple testing apparatuses can provide data to build performance envelopes for the cement system under evaluation.

A user preparing and filling the testing apparatus 100 for tensile strength testing of a cement sample begins by selecting the appropriate sample container end member (e.g., end member 146) and inserting the end member 146 into pressfit engagement with the first end cap 110 of the pressure vessel 102. The end member 146 of the sample container 104 can then be bolted to the first end cap 110 of the pressure vessel 102. The tubular member 150 can then be inserted into engagement with the first end member 146 of the sample container 104. The second end member 148 of the sample container 104 can then be attached to the tubular member 150. Measurement devices as discussed above can then be attached to measure the diameter of the tubular member 150 and the distance between the end members 146, 148. The sidewall member 114 of the pressure vessel 102 can then be slid down over the components 146, 148, 150 of the sample container 104. The sidewall member 114 can then be attached to the first end cap 110 of the pressure vessel 102. At this time, the sample volume 130 of the sample container 104 can be filled with the cement slurry to be tested. The piston 106 can then be placed in position and bolted to the second end member 148 of the sample container 104. The lower port 126 in the sidewall member 114 can be used to fill the portion of the working volume 108 of the pressure vessel 102 outside of the sample container 104 with a temperature-stable pressurizing fluid (e.g., water). Air being displaced by the pressurizing fluid can be vented through the upper port 126 in the sidewall member 114. The isolation ring 115 and the second end cap 112 of the pressure vessel 102 can then be installed.

A user preparing and filling the testing apparatus 100 for tensile strength testing of a cement sample mixed at other than ambient conditions uses a generally similar process to the previously discussed tensile strength testing preparation. However, the piston 174 and associated end cap 184 are used rather than piston 106 and end cap 112. After the testing apparatus 100 is assembled, the sample volume 130 of the sample container 104 and the working volume 108 of the pressure vessel 102 can be filled with the pressurizing fluid. The heated and pressurized cement slurry can be pumped into the sample volume 130 through channel 175 in the piston 174. This approach allows mixing a slurry of the cement sample at pressure conditions that are different than ambient pressure conditions; and then transferring the slurry of the cement sample to the sample container for curing without exposure to ambient pressure conditions.

A user preparing and filling the testing apparatus for compressive strength testing of a cement sample mixed at ambient conditions uses a generally similar process to the previously discussed tensile strength testing preparation for a sample mixed at ambient conditions. However, end members 164, 166 rather than end members 146, 148 are used for the sample container 104. The sample volume 130 is filled through the buffer space 182. The cement slurry can be added to the sample container 104 to fill the tubular member 150 and part of the buffer space 182. The buffer space 182 can compensate for the expansion or shrinkage of the cement sample during curing and increase the likelihood that the interior of the tubular member 150 is full when testing begins.

A user preparing and filling the testing apparatus 100 for compressive strength testing of a cement sample mixed at other than ambient conditions uses generally similar process. The sample container 104 is assembled with the compressive strength testing end members 164, 166. The pressurizing slurry piston 174 is used with the associated end cap 184 of the pressure vessel 102.

Cements shrinkage and/or expansion can be monitored during curing by directly measuring the size of the sample and/or by volumetric measurements based on the amount of fluids provided to the working volume 108 of the pressure vessel 102 and the sample volume 130 of the sample container 104. The volume of fluid provided to the working volume 108 of the pressure vessel 102, or the changes in the measurements of sample size, can provide an indication of bulk shrinkage. The volume of fluid provided to the sample volume 130 of the sample container 104 can provide an indication of chemical shrinkage.

Figure 5:
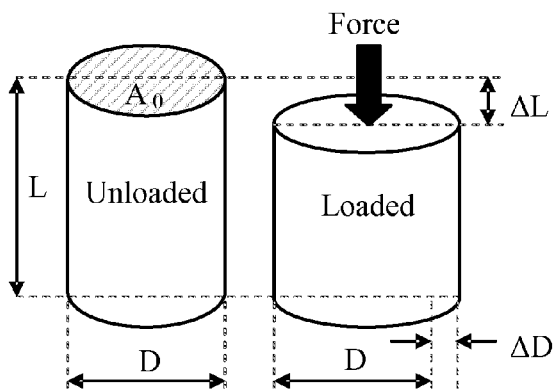
FIG. 5 is a schematic of compressive testing of a cement sample.

The testing apparatuses 100 can be used to perform both compressive and tensile strength tests. Compressive tests are performed by applying an axial compressive force to the sample as shown in FIG. 5. In contrast, direct tensile strength tests are performed by applying an axial pulling force on the sample. In either compressive or tensile strength tests, the force is gradually increased until the cement sample has failed, or seen the maximum amount of force available has been applied. Measurements are made of the force, axial deformation ($\Delta L$), and diametric deformation ($\Delta D$). From this information the engineering parameters normal stress ($\sigma$), axial strain ($\epsilon a$), lateral strain ($\epsilon l$), Young's Modulus (YM) and Poisson's Ratio (PR) as well as the compressive strength (CS) can be determined.

Normal stress is defined as a force applied perpendicular to a unit of area. Axial strain is defined as the amount of dimensional change ($\Delta L$) relative to the original length (L0) in the direction of primary stress. Lateral strain is defined as the amount of dimensional change ($\Delta D$) relative to the original Diameter (D0) in a direction perpendicular to the primary stress.

Figure 6:
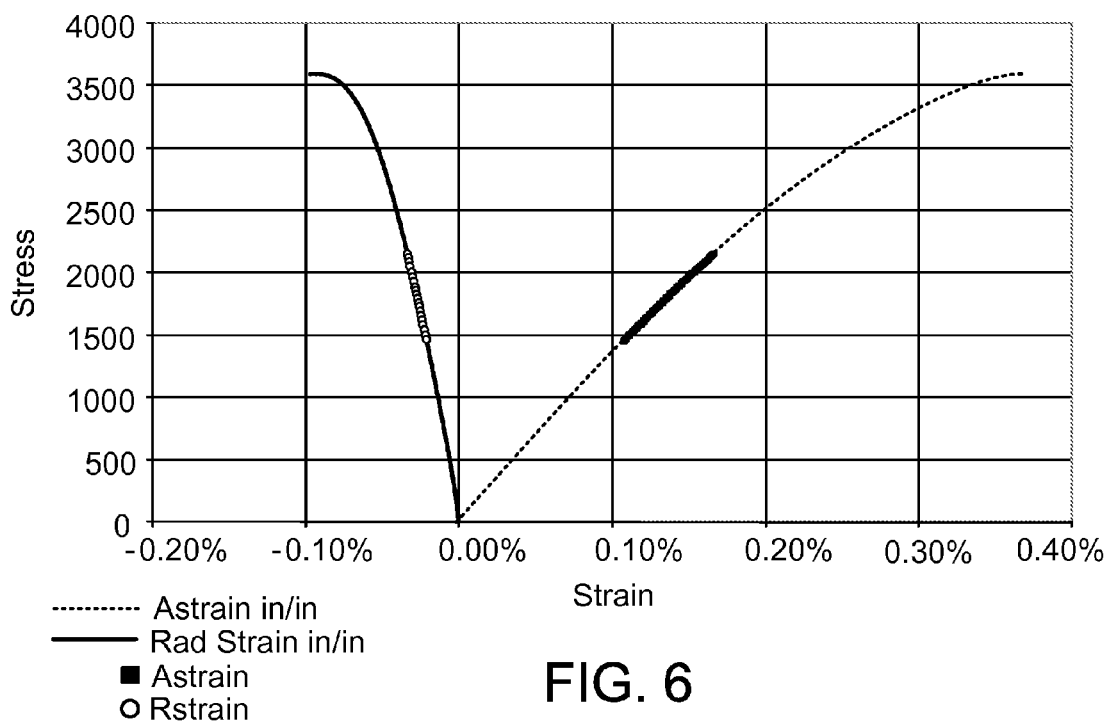
FIG. 6 is a chart representing results of compressive testing of a cement sample.

The results of cement compressive tests can be presented as stress versus strain as shown in FIG. 6. In rock mechanics, compressional stress is typically defined as positive; thus, a reduction in dimension is presented as a positive strain. For the example stress-strain curve, the positive strain ($\epsilon$) portion of the x-axis is equivalent to the axial strain ($\epsilon a$). The curve associated with positive strain is measured and mathematically derived from the axial deformation and pressure sensors in an individual testing apparatus 100. When cement is deformed axially in compression, it has the tendency to expand in the lateral direction. This results in a strain value that is negative. The curve associated with the negative strain values, or lateral strain ($\epsilon l$) is derived from the diametric deformation and pressure sensors in an individual testing apparatus 100.

Young's Modulus (YM) is a measure of the stiffness of an isotropic elastic material and is defined as the ratio of the axial stress over the axial strain in the range of stress in which the material has a tendency to deform linearly under stress. In moderate stress levels, cement typically deforms linearly and therefore its modulus is often reported. The Young's Modulus of a cement sample is determined experimentally by taking the slope of a linear regression on the stress-strain plot over a known stress range (see, e.g., the darkened portion of the positive strain curve in FIG. 6). In other methods, the Young's Modulus can be derived on different portions of the stress-strain curve or from zero to a point along the stress-strain curve.

Poisson's Ratio, which characterizes the lateral deformation as a function of axial deformation is the ratio, when a sample object is stretched, of the contraction or transverse strain (perpendicular to the applied load), to the extension or axial strain (in the direction of the applied load). The Poisson's Ratio of a cement sample is determined experimentally by calculating the ratio of lateral strain change to axial strain change experienced over the same stress range.

The unconfined compressive strength is the maximum stress that cement can endure when the confining pressure (e.g., the pressure in the working volume 108 of the pressure vessel 102 outside of the sample container 104) is zero. It is determined experimentally by destructively testing the cement. The maximum stress recorded at failure is the unconfined compressive strength.

Figure 7:
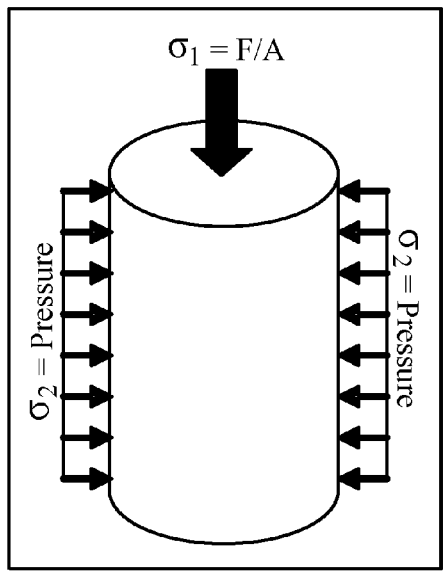
FIG. 7 is a schematic of confined compressive testing of a cement sample.

Compressive testing can also be performed with stresses applied in more than one direction. For example, a confining pressure can be used to apply fluid pressure on the lateral side surfaces of a sleeved test specimen as shown in FIG. 7. This results in a stress ($\sigma 2$) along the curved surface equal to the fluid pressure. The primary stress ($\sigma 1$) can still be applied mechanically through the hydraulic system. The unconfined compression test is a simplified version of the triaxial test with the confining pressure ($\sigma 2$) left equal to zero. The engineering parameters, previously discussed, can also be determined for a test result where the stress-strain relationship is recorded.

Figure 8:
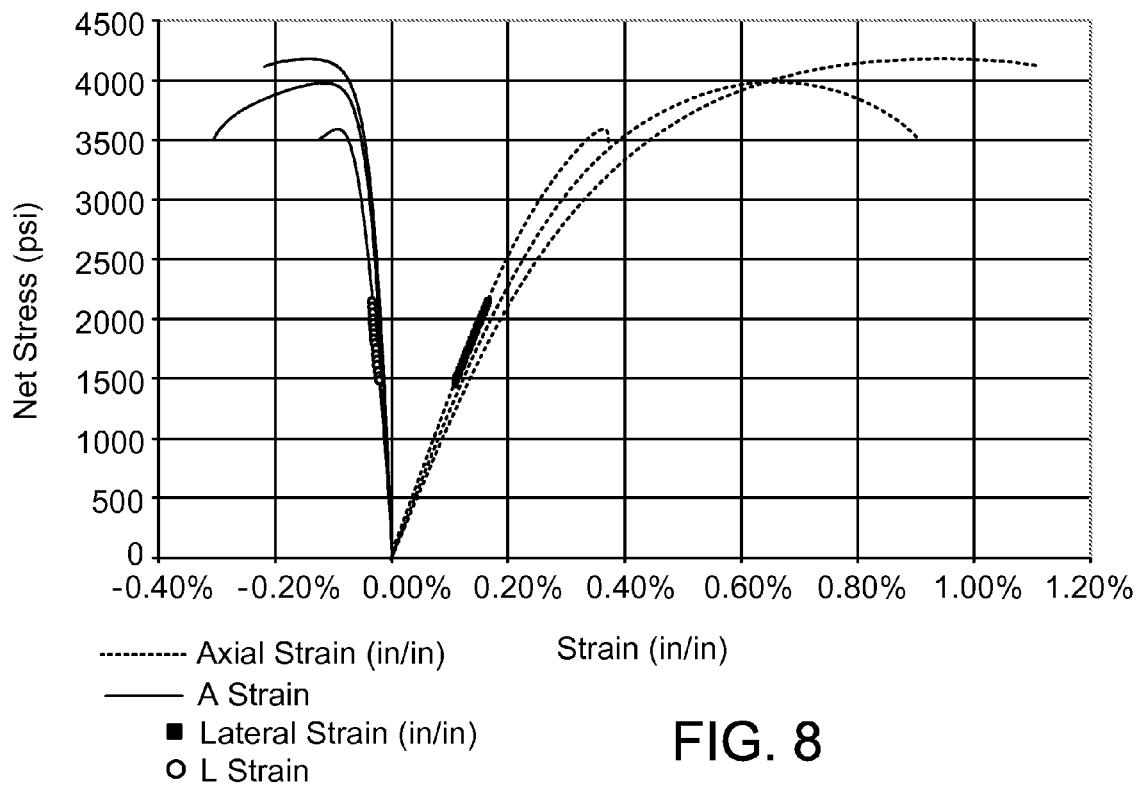
FIGS. 8 and 9 are charts representing results of compressive testing with various confining loads.

Initially, in confined compressive strength testing the fluid pressure ($\sigma 2$) and the mechanical load ($\sigma 1$) are simultaneously brought to a predetermined value for the confining pressure. Then the mechanical load ($\sigma 1$) is increased (or decreased depending on load direction) until sample failure occurs (while the confining pressure ($\sigma 2$) is held constant). The maximum load the sample withstands minus the confining stress ($\sigma 2$) is defined as the confined compressive strength. The material response and failure limits are influenced by various confining loads. For example, FIG. 8 illustrates exemplary compressive test results at three confining pressures: 0 (or unconfined), 500, and 1,000 psi. The slope of the linear portion of the stress-strain curves change marginally while the ultimate stress experienced is greatly different. As confining pressure increases, the compressive strength increases.

Figure 9:
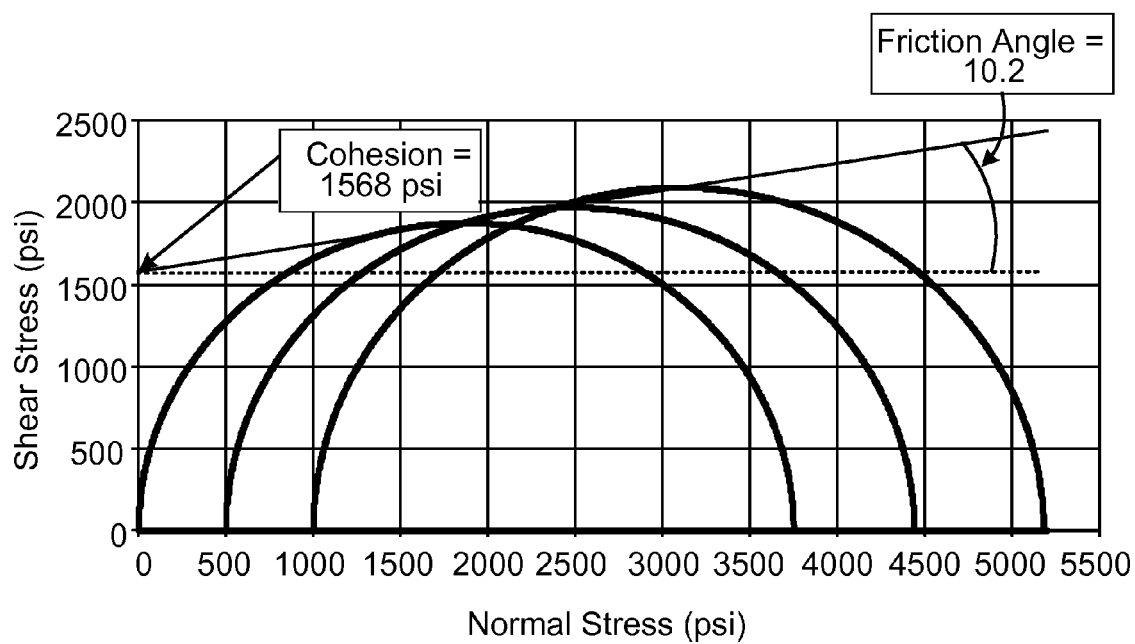

Stress at a point in a solid body has both shear and normal stress components. Analysis of the stress-state in the simple test specimen exposed to normal stresses of $\sigma 1$ and $\sigma 2$ at the boundary actually results in both shear and normal stresses at points within the sample. The transformation equation relating the shear and normal stresses takes the form of "Mohr's circle." This concept is important for cement testing because physical observations of failed samples subjected to normal stresses are found to actually fail in shear. This is especially true when cement is tested in a confined state. As shown on FIG. 9, Mohr's circle for a confined compressive test can be plotted as a half-circle on stress-strain plot in which the confining pressure ($\sigma 2$) for the test is the beginning of each half circle and the maximum stress at failure ($\sigma 1$) for the test is the end of each half circle. Each circle has a radius equal to ($\sigma 1 - \sigma 2$)/2 which is also the maximum shear stress experienced during the test or failure limit of the test.

A failure envelope can be defined by performing several confined tests each yielding a Mohr-circle. The failure limit for each case is used to establish a failure envelope which is defined by the Mohr-Coulomb shear failure line or similar model. This line's y-intercept is the "Cohesion" of the sample and the slope is the "Friction Angle" of the sample. A linear regression of the maximum axial stress ($\sigma 1$) versus the confining stress ($\sigma 2$) is used to determine the friction angle and cohesive strength. The slope, $\alpha$, of the linear least squares fit is used to calculate friction angle ($\Phi$) while the cohesive strength (S0) is determined using Unconfined Compressive Strength and the friction angle. Subsequently, a stress state represented by a Mohr-Circle can be compared to the Mohr-Coulomb shear failure envelope. If the circle crosses the envelope, then a shear failure is expected.

The maximum "pulling" stress that a cement sample can withstand is defined at the tensile strength (TS). The tensile strength of a sample can be tested indirectly or directly. Direct testing (e.g., by actually pulling on the sample until it breaks) can provide different, possibly more accurate results than indirect testing. However, direct testing typically requires removing the sample from the pressure vessel in which it has been cured.

The results of tensile strength testing can be plotted on stress-strain curves and analyzed in similar fashion to that discussed above for analyzing the results of compressive testing.

Multiple testing apparatuses 100 can be attached to the pressure sources 176, 178, 180 as shown in FIG. 4. The valves can all be opened and in the pressure sources 176, 178, 180 used to bring the system to an initial pressure for curing. As discussed above, the temperature of the system can also be controlled. Depending on the specific test being conducted, an individual testing apparatus 100 may be brought to curing pressure before receiving the cement sample or may be brought to curing pressure after receiving the cement sample to be tested. After initial temperature and pressure conditions are set, the cement samples can be cured for a desired period of time (e.g., 8-72 hours, up to 14 days, or up to 6 months). Testing can be preformed on semisolid (e.g., partially cured) or solid (e.g., cured) samples.

After the cement samples have been cured for the desired period of time, the tests can be performed. The valves V0.1 and V0.2 can be closed to isolate the pumps 176, 178, 180 from each other. All valves, except the valves associated with the particular testing apparatus 100 being used to perform the current test, can be closed to lock in pressure in the other testing apparatuses 100. The pumps 176, 178, 180 can then be operated to perform the test that the particular testing apparatus 100 is configured for by controlling the pumps as indicated in (but not limited to) Table 1. In particular, the load pressure can be increased or decreased as indicated in Table 1 until the cement sample fails. Failure of the cement sample can be indicated, for example, by a sudden change in sample dimensions.

The system can include a control system operable to automatically control pumps 176, 178, 180, valves, and heating mechanisms to carry out specified tests. In some cases, pumps 176, 178, 180, valves, and heating mechanisms can be manually operated. Data from the instrumentation can be recorded using a data acquisition system and used for control of the system.

TABLE 1

| Name | Insitu Uniaxial Compressive Strength | Insitu Triaxial Compressive Strength #1 | Insitu Triaxial Compressive Strength #2 | Insitu Uniaxial Tensile Strength | Insitu Hydrostatic Strength |
|---|---|---|---|---|---|
| Confinement Pressure (Pump #2) | $=\sigma 0$* | $>\sigma 0$ | $\neq \sigma 0$ | $=\sigma 0$ | =Pump #1 |
| Load Pressure Direction (Pump #1) | Increasing from $\sigma 0$ | Increasing from $\sigma 0$ | Increasing from $\sigma 0$ | Decreasing from $\sigma 0$ | Increasing from $\sigma 0$ |
| Pore Pressure (Pump #3) | $=\sigma 0$ | $=\sigma 0$ | $=\sigma 0$ | $=\sigma 0$ | $=\sigma 0$ |

*where $\sigma 0$ is the initial pressure used during curing.

The configuration of testing apparatuses 100 allow the pore pressure to be controlled separately from the confining pressure. Accordingly, the pore pressure can be maintained at the curing pressure, set equal to the confining pressure, or set at another arbitrary value. This allows the user replicate tests with different pore and confining pressures to verify that the tensile strength/compressive strength of the sample is not affected by the relationship between pore and confining pressures.

The methods and systems described can allow a liquid slurry to cure at pressure and temperature conditions and, while curing or after cured, to be tested for volume changes, the mechanical response of the sample, and failure limits without removing curing, or cured, cement from the testing apparatus. Testing in the curing vessel can reduce the possibility that removal of the sample from the testing apparatus could impart damage to the sample that would influence subsequent results. Testing in the curing vessel can also save time and money, and reduces the limits on the ability to test curing in a small time window relative to cure associated with systems which require removal of the curing vessel for testing.

The methods and systems described can allow for independent control over pore pressure, confining pressure, and load magnitude, direction, and rate. In combination, the independent control of these parameters allows for multiple samples to be tested in replicate and with changes to one parameter at a time to provide statistics as well as different testing conditions.

The methods and systems described can provide the ability to cure and test cement at conditions that represent a cemented well casing.

A number of embodiments have been described. Nevertheless, it will be understood that various modifications may be made. For example, in some embodiments, the upper end member of the sample container is provided by the piston and the lower end member of the sample container is provided by the lower end cap of the pressure vessel. Accordingly, other embodiments are within the scope of the following claims.

What is claimed is:

1. A device for testing cement, the device comprising:
a pressure vessel that comprises an interior working volume; and
a sample container located within the interior working volume and having wall segments that define a first interior volume coupled to a first piston that are slidable with respect to the interior working volume, and that define a second interior volume having a second piston slidable within the second interior volume, and an aperture extending through a wall segment of the first interior volume and connecting the first and second interior volumes, the pressure vessel configured to supply a first pressurized fluid to control a pore pressure of a cement sample and to supply a second pressurized fluid to lateral exterior surfaces of the sample container to provide independent control of the confining pressure and the pore pressure.

2. The device of claim 1, further comprising:
a substantially tubular sleeve that defines the lateral exterior surfaces of the second interior volume of the sample container;
a first end member attachable to a first end of the substantially tubular sleeve; and
a second end member attachable to a second end of the substantially tubular sleeve that is opposite the first end, wherein the substantially tubular sleeve comprises a material that is more flexible than a material of the first and second end members.

3. The device of claim 2, wherein the material of the substantially tubular sleeve comprises rubber, and the material of the first and second end members comprises stainless steel.

4. The device of claim 3, wherein the first and second end members are configured to grip opposite ends of the cement sample, the device further comprising:
a testing assembly attachable to the first and second end members and configured to apply axial tension to the cement sample through the first and second end members while maintaining the cement sample at a particular pressure condition.

5. The device of claim 1, further comprising:
a first pressure source fluidly coupled to an interior volume of the sample container, the first pressure source configured to control a pressure of the first pressurized fluid; and
a second pressure source fluidly coupled to the interior working volume, the second pressure source configured to control a pressure of the second pressurized fluid.

6. The device of claim 5, wherein at least one of the first or second pressure sources comprises a pump.

7. The device of claim 5, wherein the pressure of the second pressurized fluid is controllable to simulate a condition of a subterranean zone.

8. A cement testing system, comprising:
a plurality of cement testing devices, each device comprising:
a pressure vessel that encloses a working volume; and
a sample container located within the interior working volume and having wall segments that define a first interior volume coupled to a first piston that are slidable with respect to the interior working volume, and that define a second interior volume having a second piston slidable within the second interior volume, and an aperture extending through a wall segment of the first interior volume and connecting the first and second interior volumes, the pressure vessel configured to supply a first pressurized fluid to control a pore pressure of a cement sample and to supply a second pressurized fluid to lateral exterior surfaces of the sample container to provide independent control of the confining pressure and the pore pressure;
a first conduit that fluidly couples each of the cement testing devices to the first pressurized fluid;
a second conduit that fluidly couples each of the cement testing devices to the second pressurized fluid; and
a control system communicably coupled to one or more valves positioned in the first and second conduits.

9. The cement testing system of claim 8, further comprising:
a plurality of pumps fluidly coupled with the cement testing devices through at least one of the first or second conduits, the plurality of pumps communicably coupled with the control system.

10. The cement testing system of claim 9, wherein the control system is configured to selectively open the one or more valves to set each cement sample of the plurality of cement testing devices to an initial pressure for curing.

11. The cement testing system of claim 9, wherein the control system is configured to selectively control the one or more valves and the plurality of pumps to maintain each of the plurality of cement samples at a unique pore pressure.

12. The cement testing system of claim 11, wherein the control system is configured to selectively control the one or more valves and the plurality of pumps to maintain each of the plurality of cement samples at a unique confining pressure.

13. The cement testing system of claim 9, wherein the control system is configured to selectively adjust the one or more valves to fluidly isolate one or more of the plurality of pumps from the plurality of cement testing devices.

14. The cement testing system of claim 8, further comprising:
a plurality of heating apparatuses coupled with the plurality of cement testing devices and communicably coupled with the control system, wherein the control system is configured to adjust respective temperatures of the plurality of cement samples with the plurality of heating apparatuses.

* * * * *